United States Patent
Brunzel et al.

(10) Patent No.: US 11,472,760 B2
(45) Date of Patent: *Oct. 18, 2022

(54) METHOD FOR PREPARING UNSATURATED MACROCYCLIC KETONES (II)

(71) Applicant: SYMRISE AG, Holzminden (DE)

(72) Inventors: Tom Brunzel, Rostock (DE); Angela Köckritz, Berlin (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/421,536

(22) PCT Filed: Jan. 17, 2019

(86) PCT No.: PCT/EP2019/051091
§ 371 (c)(1),
(2) Date: Jul. 8, 2021

(87) PCT Pub. No.: WO2020/147951
PCT Pub. Date: Jul. 23, 2020

(65) Prior Publication Data
US 2022/0055976 A1 Feb. 24, 2022

(51) Int. Cl.
*C07C 45/34* (2006.01)
*B01J 23/00* (2006.01)
*B01J 23/44* (2006.01)
*B01J 23/745* (2006.01)

(52) U.S. Cl.
CPC .............. *C07C 45/34* (2013.01); *B01J 23/44* (2013.01); *B01J 23/745* (2013.01); *C07C 2601/18* (2017.05)

(58) Field of Classification Search
CPC ......... C07C 45/34; B01J 23/44; B01J 23/745; B01J 31/2226
See application file for complete search history.

(56) References Cited

U.S. PATENT DOCUMENTS 8,507,728 B2 * 8/2013 Kaneda ................. C07C 45/34
568/360
2011/0288340 A1 11/2011 Kaneda

FOREIGN PATENT DOCUMENTS

EP 2364965 A1 9/2011
JP H069481 A1 1/1994

OTHER PUBLICATIONS

Mookherjee B D et al: "Synthesis of racemic muscone and cyclopentadecanone (exaltone) from 1,9-cyclohexadecadiene", Journal of Organic Chemistry, American Chemical Society, US, vol. 36, No. 22, Jan. 1, 1971 (Jan. 1, 1971), pp. 3266-3270.
International European Search Report and Written Opinion dated Sep. 20, 2019.

* cited by examiner

*Primary Examiner* — Sikarl A Witherspoon
(74) *Attorney, Agent, or Firm* — Dilworth & Barrese, LLP

(57) ABSTRACT

A process is proposed for preparing unsaturated macrocyclic monoketones, comprising the following steps:
(a) providing macrocyclic dienes having a ring size of at least 9 carbon atoms;
(b) contacting the starting materials from step (a) with
  (b1) a palladium(II) salt and/or a palladium(II) complex; and
  (b2) an oxidizing agent; and
  (b3) a solvent; and optionally
  (b4) a ligand; and optionally
  (b5) a co-catalyst; and optionally
  (b6) an acid,
with the proviso that the co-catalyst (b5) comprises or consists of a divalent or trivalent iron salt which is different from $FeSO_4$ and is preferably iron(III) nitrate.

20 Claims, 2 Drawing Sheets

METHOD FOR PREPARING UNSATURATED MACROCYCLIC KETONES (II)

This application claims priority to International Application No. PCT/EP2019/051091 filed on Jan. 17, 2019.

FIELD OF THE INVENTION

The invention is located within the field of the preparation of unsaturated macrocyclic monoketones from macrocyclic dienes in a single-stage oxidation in the presence of an oxidizing agent, a palladium(II) salt and/or a palladium(II) complex, a co-catalyst, and a solvent.

TECHNOLOGICAL BACKGROUND

Ketones are suitable as solvents and chemical raw materials, and are therefore used in a variety of areas. Such ketones are generally prepared by two-stage reaction processes, in which an alcohol generated by hydration of an olefin is dehydrogenated. Simpler processes have become known in the meantime, including single-stage reaction processes in which an olefin is oxidized directly.

Two-stage processes for preparing macrocyclic monoketones are known from the prior art. The industrial synthesis of macrocyclic ketones is accomplished, for example, via selective monoepoxidation and rearrangement of the epoxide to the ketone in the presence of halides of alkali metals or alkaline earth metals, as described in B. D. Mookherjee, R. W. Trenkle, R. R. Patel, *J. Org. Chem.* 36 (1971), 3266. Reduction of the epoxy group to a hydroxyl group, followed by subsequent oxidation to the ketone, is described for example in U.S. Pat. No. 3,718,696.

The Wacker process, using a $PdCl_2/CuCl_2$ catalyst, is known as one of the processes for direct oxidation of an olefin. This process is effective in the oxidation of terminal olefins each having a carbon-carbon double bond (abbreviated hereinafter to "C=C bond") at one end of a molecule. This process, however, achieves only low reactivity when used for the oxidation of internal olefins, each having a C=C bond at a position other than their ends. The results achieved in this process when the number of carbon atoms in the starting material is increased are also unsatisfactory, owing to a significant drop in the reaction rate. For this reason, in the industrial sector, the use of the Wacker process is confined only to the production of lower carbonyl compounds such as acetaldehyde and acetone, which are obtained by oxidation of lower terminal olefins.

RELEVANT PRIOR ART

Kaneda et al. developed a method requiring no co-oxidant for the reoxidation of Pd(0), instead using oxygen for direct reoxidation of Pd(0) to Pd(II). This method uses a dimethylacetamide/$H_2O$ mixture at 80° C. (T. Mitsudome, T. Umetani, N. Nosaka, K. Mori, T. Mizugaki, K. Ebitani, K. Kaneda, *Angew. Chem. Int. Ed.* 45 (2006) 481). This process also allows the oxidation of linear internal olefins and cyclic olefins, an example being cyclohexene (T. Mitsudome, K. Mizumoto, T. Mizugaki, K. Jitsukawa, K. Kaneda, *Angew. Chem. Int. Ed.* 49 (2010) 1238). The only successful catalysts in this case, however, have been chlorine-containing palladium catalysts. In-house studies have shown that this method only achieves inadequate yields of the desired ketones when starting from macrocyclic olefins and dienes as substrates, even when using a co-oxidizing agent.

A further variation of the Wacker oxidation of olefins, using cationic palladium complexes, is described in US 20140194604. In this case, however, the starting substrates used are not macrocyclic dienes.

Similarly, WO 2010 061807 describes a modification of the Wacker process, in which the starting substrates employed include macrocyclic dienes. In this case, however, the only dienes described have a maximum ring size of 8 carbon atoms.

Subject matter of EP 2364965 A1 (KANEDA), furthermore, is a process for preparing ketones by oxidizing olefins (e.g., cyclooctene) with oxygen in the presence of Pd catalysts in amidic solvents. Pd catalysts contemplated include the halides and also their complexes with the amidic solvents, but not Pd-ligand systems.

OBJECT OF THE INVENTION

Macrocyclic dienes form a chelate complex with Pd(II) species/compounds. As a result of the physical arrangement of the ligand and its flexibility, however, further coordination of the reacting components is hindered, thereby severely limiting the activity and selectivity of the reaction. This is one of the reasons why such macrocyclic dienes only react very poorly in the processes known from the prior art. A further, exacerbating factor is that these highly apolar macrocyclic dienes have only limited solubility in polar solvents. Satisfactory yields, therefore, are not achievable with the processes known from the prior art.

It was an object of the present invention, therefore, to provide a process which overcomes the disadvantages of the prior art. The specific object was to provide a process which enables a simple regime, sparing in its use of materials and energy and therefore sustainable, yet which at the same time achieves economic yields.

DESCRIPTION OF THE INVENTION

A process is provided for preparing unsaturated macrocyclic monoketones, comprising the following steps:
(a) providing macrocyclic dienes having a ring size of at least 9 carbon atoms;
(b) contacting the starting materials from step (a) with
  (b1) a palladium(II) salt and/or a palladium(II) complex; and
  (b2) an oxidizing agent; and
  (b3) a solvent; and optionally
  (b4) a ligand; and optionally
  (b5) a co-catalyst; and optionally
  (b6) an acid, preferably an acid with a weakly coordinating anion or an inorganic salt with a weakly coordinating anion,
with the proviso that the co-catalyst (b5) comprises or consists of a divalent or trivalent iron salt which is different from $FeSO_4$ and is preferably iron(III) nitrate.

Surprisingly it has been found that the process identified above can be used to prepare unsaturated macrocyclic monoketones in significantly higher yields than was known hitherto from the prior art or could have been anticipated. Likewise, a commercial use of the resulting isomers is possible, so making the process exceptionally sustainable and efficient.

A further advantage of the invention is that the macrocyclic dienes are reacted so effectively by the process of the invention that even if the macrocyclic dienes take the form of a mixture of E,E, E,Z and Z,Z isomers, each having a different reactivity, these isomers can be oxidized selectively to form a monoketone without the formation of unwanted amounts of diketones.

BRIEF DESCRIPTION OF THE DRAWINGS

The present invention will be described in greater detail with reference to the accompanying drawings, in which FIG. 1 schematically illustrates the equation forming the process according to the present invention.

DETAILED DESCRIPTION OF THE INVENTION

Figure 1:
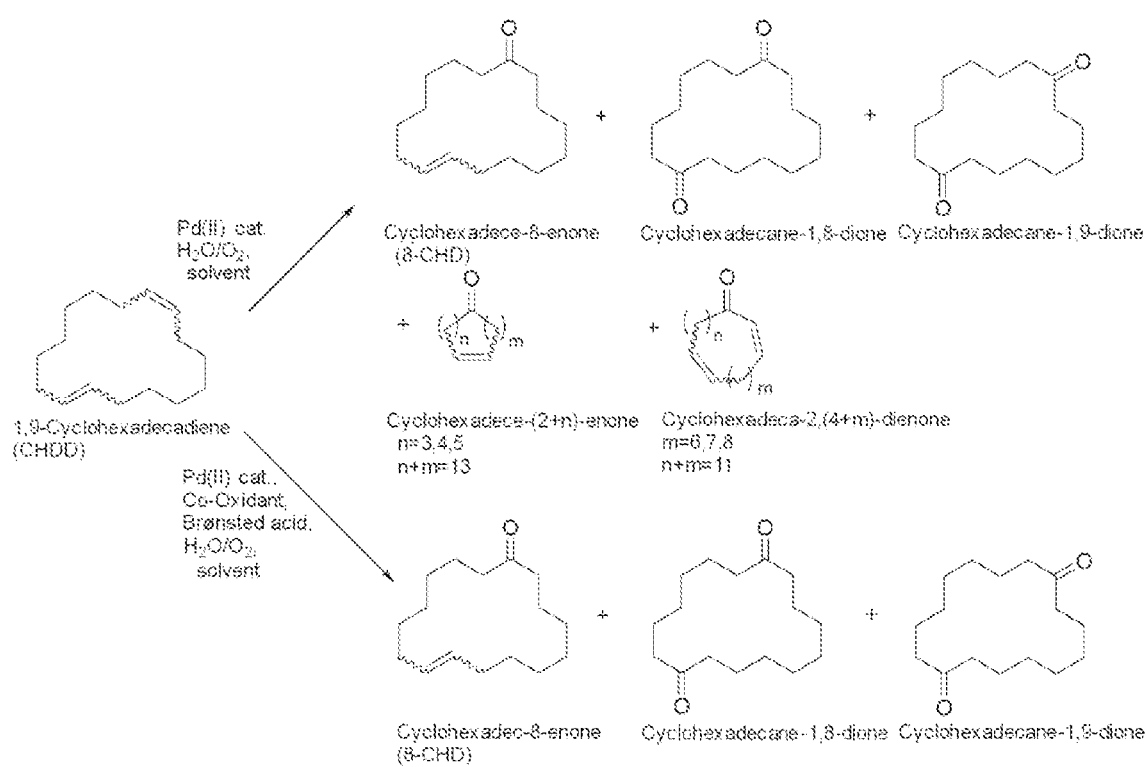

FIG. 1 illustrates by way of example the course of the preparation process of the invention. This figure, however, represents only one example and is in no way intended to be limiting.

The macrocyclic diene (a) preferably comprises two non-conjugated double bonds. In one preferred embodiment of the invention the macrocyclic diene has a ring size of 9 to 30 carbon atoms, preferably of 12 to 18 carbon atoms and more preferably of 16 carbon atoms. In one particularly preferred embodiment the macrocyclic diene (a) is 1,9-cyclohexadecadiene (CHDD).

In another preferred embodiment of the process of the invention, the macrocyclic diene (a) used is a mixture of various stereoisomers. In one particularly preferred embodiment of the process of the invention, the macrocyclic diene (a) is 1,9-cyclohexadecadiene (CHDD) and takes the form of a mixture of E,E, E,Z and Z,Z isomers.

The preparation process of the invention is used preferably for preparing cyclohexadec-8-enone (8-CHD). In one particularly preferred embodiment of the invention the macrocyclic diene (a) used is CHDD, and the preparation process of the invention yields 8-CHD.

In a first embodiment of the invention, the solvent (b3) is a polar aprotic solvent. The solvent (b3) in this case is preferably from the group consisting of N,N-disubstituted open-chain and cyclic acid amides, as for example dimethylformamide, dimethylacetamide, diethylacetamide, dimethylpropionamide, N-methylpyrrolidone, aliphatic, cycloaliphatic or aromatic nitriles such as acetonitrile, propionitrile or benzonitrile, or linear and cyclic ethers, cyclic lactones and carbonates.

Preferably, in a first embodiment of the invention, small amounts of water are added to the solvent (b3). A preferred amount is from 0.1 to 25 vol %, more preferably an amount of 1-20 vol % and very preferably an amount of 5-15 vol %. The volume percentages here are based on the solvent (b3).

Furthermore, in a first embodiment of the invention, the ligand (b4) is necessarily present in the process of the invention. The ligand is preferably a bidentate ligand. The use of a bidentate ligand is therefore advantageous firstly because it possesses such strong donor properties that it is able to carry out molecular stabilization of the palladium(II) salt and/or the palladium(II) complex and hence is able to prevent precipitation of palladium(0). On the other hand, the ligand may possess bulky substituents which prevent chelation of palladium by the starting material (a). The ligand preferably comprises N,N, N,O, N,S and/or O,O donor atoms. More preferably the ligand comprises N,N, N,O and/or O,O donor atoms. These atoms may be part of a cyclic system or may be joined to one another via other suitable bridging groups.

Figure 2:
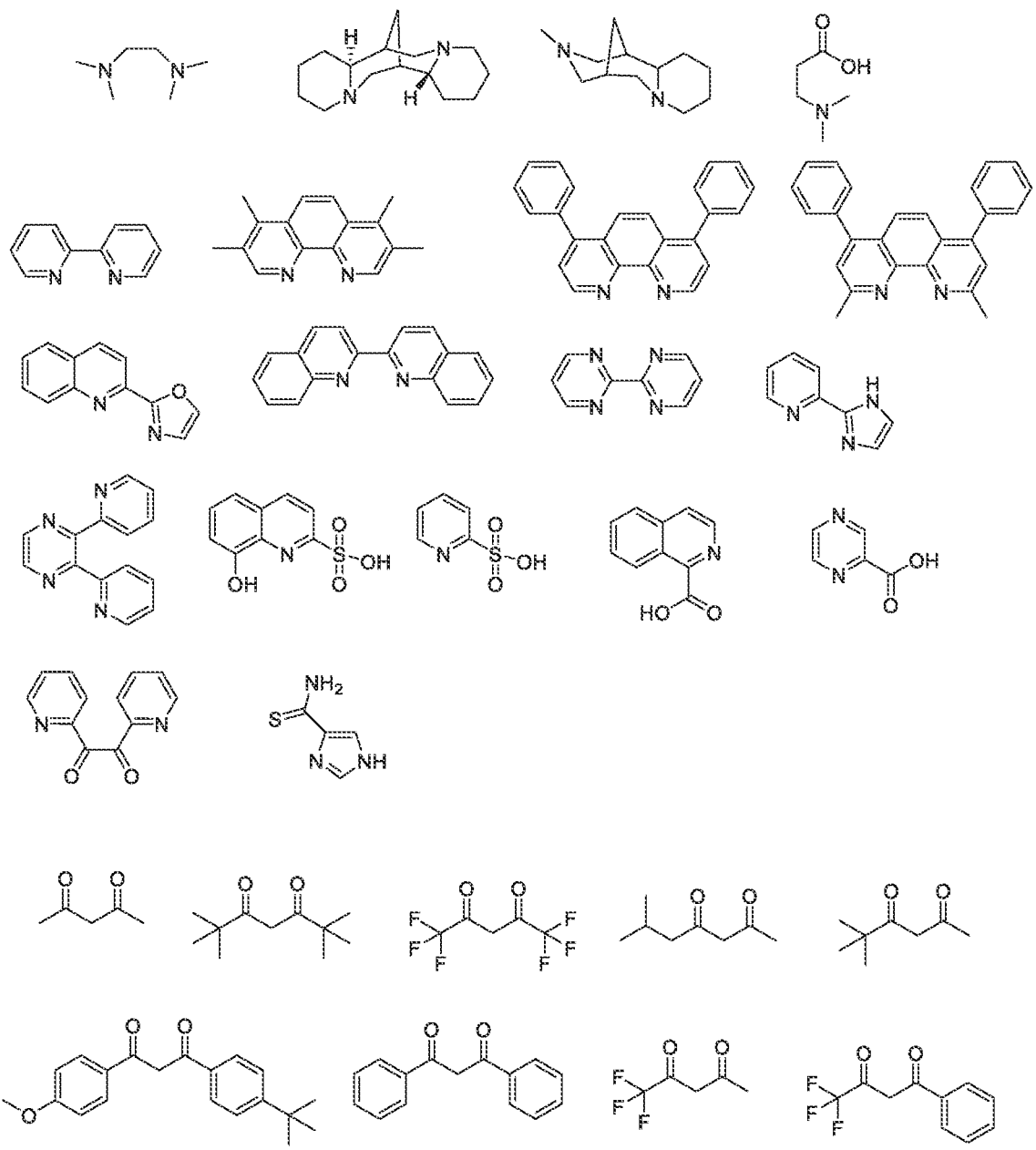
FIG. 2 illustrates certain compounds which are used in the process according to the invention.

FIG. 2 illustrates bidentate ligands which are used for one embodiment of the process of the invention. This figure is illustrative and is not intended to represent any limitation.

The palladium(II) salt and/or the palladium(II) complex (b1) are selected, in a first embodiment of the process of the invention, from the group consisting of palladium bromide, palladium acetate, palladium trifluoroacetate, palladium benzoate, tetrakis(acetonitrile)palladium(II) tetrafluoroborate, tetrakis(acetonitrile)palladium(II) bis(trifluoromethanesulfonate), palladium nitrate and/or palladium sulfate.

Furthermore, a first embodiment of the process of the invention is characterized in that the palladium(II) salt and/or the palladium(II) complex (b1) form, with the bidentate ligand (b4), a palladium compound of the formula (I) and/or of the formula (II)

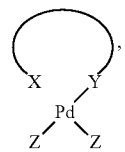

where X and Y each independently of one another are N,N, O,N or O,O; and
where Z independently at each occurrence is a halogen, acetate, trimethylacetate, trifluoromethylacetate, MeCN, PhCN, $NO_2$, NO, nitrate, nitrite or sulfate;

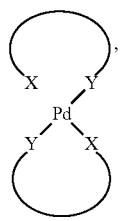

where X and Y each independently of one another are O,O, N,N or O,N.

The palladium compound thus obtained is present, in a first embodiment of the invention, at a concentration of 0.01 to 25 mol %, preferably of 1 to 20 mol %, more preferably of 1 to 15 mol % and very preferably of 1 to 5 mol %. The mol % figures are based in each case on the starting material (a).

For the palladium compound, in a first embodiment of the invention, a neutral palladium catalyst is preferred.

The palladium compounds of the formulae (I) and/or (II) may be formed either in situ or in a separate preparation process ex situ. In the case of a separate, ex situ preparation, the palladium compounds directly, rather than the palladium (II) salt and/or the palladium(II) complex (b) and the ligands (b4), are contacted with the starting material (a) of the preparation process of the invention.

In a first embodiment of the invention an oxygen-containing gas is used as oxidizing agent (b2). The oxygen-containing gas preferably comprises oxygen at a concentration of 1 to 100 vol %, more preferably of 5 to 100 vol % and most preferably of 21 to 100 vol %.

Furthermore, in a first embodiment, the process of the invention is carried out at elevated temperatures. Preferred temperatures are from 50° C. to 120° C., more preferably from 60° C. to 100° C., most preferably from 70° C. to 90° C.

In a second embodiment of the invention the solvent (b3) is a polar aprotic solvent. In this case the solvent (b3) is preferably from the group consisting of N,N-disubstituted open-chain and cyclic acid amides, as for example dimethylformamide, dimethylacetamide, diethylacetamide, dimethylpropionamide, N-methylpyrrolidone, aliphatic, cycloaliphatic or aromatic nitriles such as acetonitrile, propionitrile or benzonitrile, or linear and cyclic ethers, cyclic lactones and carbonates.

In the context of the invention the use of the singular such as "a" or "an" or "the" may also include the plural, unless something different is clearly apparent from the context. For example, the term "the solvent" may also include a multiplicity of solvents, including mixtures thereof, such as a solvent mixture, for example.

In a second embodiment of the invention, small amounts of water are preferably added to the solvent (b3). A preferred amount is from 0.1 to 25 vol %, more preferably an amount of 1-20 vol % and very preferably an amount of 5 to 15 vol %. The volume percentages here are based on the solvent (b3).

Furthermore, in a second embodiment of the invention, the co-catalyst (b5) and the acid (b6) are necessarily present in the process of the invention.

Further co-catalysts (b5) that are suitable, in addition to the aforementioned iron salts—with the exception of $FeSO_4$—are, for example, quinones, heteropoly acids and polyoxometalates or metal complexes whose central metal is easily able, through oxidation with oxygen, to switch between an II/III, II/IV, IV/V or I/II oxidation state. Central metals of suitable complexes of this kind may be selected, for example, from the group of Fe, Cu, Mn, Co, Ni and V. The co-catalysts are preferably used in combinations, in order to assist and facilitate electronic transitions during the redox processes. In one preferred embodiment the co-catalysts are selected from the group consisting of benzoquinones, naphthoquinones, anthraquinones, molybdatophosphoric acid, molybdatovanadatophosphoric acids, tungstomolybdatophosphoric acids, tungstovanadatophosphoric acids, phthalocyanine complexes, CuCl, $CuCl_2$, $CuSO_4$, $VOSO_4$. In these cases a combination, for example, of $Fe(NO_3)_3$ and $FeSO_4$, in a weight ratio of 1:1, for example, is then also possible.

In a further embodiment of the invention, further oxidizing agents may also be used instead of the co-catalysts for the reverse oxidation of Pd(0) to Pd(II). These further oxidizing agents are, for example, peroxides, and may be selected from the group of $H_2O_2$, t-BuOOH and metal peroxides, and also peroxodisulfates, especially $Na_2S_2O_8$.

Likewise possible is oxidation by means of an oxygen-containing gas, with such a gas being injected preferably at an overall pressure such that the oxygen partial pressure is 1-10 bar, preferably 1-5 bar.

In a second embodiment of the invention the co-catalyst (b5) is added preferably at a concentration of 1 to 300 mol %, more preferably of 5 to 150 mol % and most preferably of 10 to 100 mol %. The mol % figures are based in each case on the starting material (a).

The acid (b6) in a second embodiment of the invention is preferably a Brønsted acid and/or a Lewis acid. Suitable Brønsted acids are inorganic mineral acids with weakly coordinating anions, and organic carboxylic, sulfonic and phosphonic acids. Sulfonic acids are particularly suitable.

The Lewis acids include compounds with an incomplete or unstable electron octette, such as $B(CH_3)_3$, $BF_3$ and $AlCl_3$, for example.

In a second embodiment of the invention the acid (b6) is added preferably at a concentration of 5 to 500 mol %, more preferably of 15 to 300 mol %, more preferably still of 30 to 200 mol % and most preferably of 50 to 150 mol %. The mol % figures are based in each case on the starting material (a).

In one preferred embodiment of the invention the acid is a Brønsted acid. The Brønsted acid is added preferably at a concentration of 5 to 500 mol %, more preferably of 15 to 300 mol %, more preferably still of 30 to 200 mol % and most preferably of 50 to 150 mol %. The mol % figures are based in each case on the starting material (a).

Furthermore, in a second embodiment of the invention, the palladium(II) salt and/or the palladium(II) complex (b1) are/is used preferably at a concentration of 0.01 to 20 mol %, more preferably of 0.5 to 10 mol % and very preferably of 1 to 5 mol %. The mol % figures are based in each case on the starting material (a).

In a second embodiment of the invention, in a preferred way, by mixing a palladium(II) salt and/or a palladium(II) complex (b1) with a Brønsted acid (b6) and a suitable solvent (b3), preferably a polar aprotic solvent, a palladium compound is formed. This palladium compound may take place either in situ or in a separate preparation process ex situ. In the case of separate, ex situ preparation, instead of the palladium(II) salt and/or the palladium(II) complex (b) and the acid (b6), the preformed palladium compounds are contacted with the starting material (a) and the co-catalyst (b5) and also with a suitable solvent (b3) of the preparation process of the invention.

In one preferred embodiment this palladium compound is a cationic palladium catalyst.

In a second embodiment of the invention the cationic palladium compound is used preferably at a concentration of 0.01 mol % to 20 mol %, preferably at a concentration of 0.5 mol % to 10 mol % and very preferably at a concentration of 1 to 5 mol %. The mol % figures here are each based on the starting material (a).

The process of the invention in a second embodiment of the invention is carried out preferably at temperatures between 0° C. and 100° C., more preferably between 0° C. and 50° C., and most preferably between 0° C. and 25° C.

Industrial Applicability

In accordance with the present invention it is possible to prepare unsaturated macrocyclic monoketones, in particular from macrocyclic dienes having a ring size of at least 9 carbon atoms, and very preferably from macrocyclic dienes having a ring size of 16 carbon atoms, which can be processed on, for example, to provide valuable fragrance, aroma or flavor compounds.

The unsaturated macrocyclic monoketones obtained by the preparation process of the invention can be purified by customary separation techniques, as for example by preparative high-performance liquid chromatography (HPLC) or fractional distillation.

EXAMPLES

Examples 1 and 2, Comparative Examples C1 to C3

DMA/MeCN/$H_2O$=4/3/1; Pd($NO_3$)$_2$·2 $H_2O$ and Variation of the Co-Catalyst in Pure Oxygen Atmosphere A closable 4 ml glass reactor with screw cap and septum was charged with a solvent system consisting of N,N-dimethylacetamide, acetonitrile and water (DMA/MeCN/$H_2O$=4/3/1; $V_{tot.}$=3 ml), and with 1,9-CHDD (isomer mixture; 44 mg; 0.2 mmol). Added to this solution were palladium(II) nitrate dihydrate (0.01 mmol; 5.0 mol %); para-toluenesulfonic acid monohydrate (76 mg; 0.4 mmol) and a co-catalyst (10-20 mol %). The reactor was closed, the septum was pierced with a disposable needle, and the system was brought into an autoclave. The autoclave was purged with oxygen and then the corresponding oxygen pressure was injected (1 bar). Thereafter the reaction mixture was stirred intensely in the autoclave at room temperature for 18 h. The autoclave was subsequently let down and the reaction solution was made up to a constant volume with tetrahydrofuran and homogenized. The reaction products were analyzed qualitatively and quantitatively using an internal standard (n-hexadecane) on a GC/MS with FID. Examples 1 and 2 are inventive; examples C1 to C3 serve for comparison. The results are compiled in Table 1.

TABLE 1

Variation of co-catalysts

| Example | Co-catalyst | Co-cat. [mol %] | $X_{1,9\text{-}CHDD}$ [%] | $S_{8\text{-}CHD}$ [%] | $S_{DIKETONE}$ [%] | $Y_{8\text{-}CHD}$ [%] |
|---|---|---|---|---|---|---|
| C1 | — | — | 26 | 81 | 19 | 21 |
| C2 | Cu($NO_3$)$_2$·3 $H_2O$ | 10 | 26 | 77 | 8 | 20 |
| C3 | Benzoquinone | 10 | 28 | 75 | 10 | 21 |
| 1 | Fe($NO_3$)$_3$·9 $H_2O$ | 10 | 41 | 72 | 8 | 29 |
| 2 | Fe($NO_3$)$_3$·9 $H_2O$ | 20 | 44 | 68 | 0 | 30 |

Examples 3 to 9

DMA/MeCN/$H_2O$; Pd($NO_3$)$_2$·2 $H_2O$; Fe($NO_3$)$_3$·9 $H_2O$ and Variation of the Solvent Ratio in Pure Oxygen Atmosphere A closable 4 ml glass reactor with screw cap and septum was charged with a solvent system consisting of N,N-dimethylacetamide, acetonitrile and water ($V_{tot.}$=3 ml), and with 1,9-CHDD (isomer mixture; 44 mg; 0.2 mmol). Added to this solution were palladium(II) nitrate dihydrate (0.01 mmol; 5.0 mol %); para-toluenesulfonic acid monohydrate (38 mg; 0.2 mmol) and iron(III) nitrate nonahydrate (8 mg; 0.02 mmol). The reactor was closed, the septum was pierced with a disposable needle, and the system was brought into an autoclave. The autoclave was purged with oxygen and then the corresponding oxygen pressure was injected (3-5 bar). Thereafter the reaction mixture was stirred intensely in the autoclave at room temperature for 18-20 h. The autoclave was subsequently let down and the reaction solution was made up to a constant volume with tetrahydrofuran and homogenized. The reaction products were analyzed qualitatively and quantitatively using an internal standard (n-hexadecane) on a GC/MS with FID. The results are compiled in Table 2.

TABLE 2

Variation of solvent ratio

| Example | DMA/MeCN/$H_2O$ | Oxygen [bar] | Time [h] | $X_{1,9\text{-}CHDD}$ [%] | $S_{8\text{-}CHD}$ [%] | $S_{DIKETONE}$ [%] | $Y_{8\text{-}CHD}$ [%] |
|---|---|---|---|---|---|---|---|
| 3 | 7/—/1 | 5 | 18 | 8 | 29 | 6 | 2 |
| 4 | 6/1/1 | 3 | 18 | 38 | 69 | 8 | 26 |
| 5 | 10/4/3 | 5 | 18 | 49 | 57 | 12 | 28 |
| 6 | 5/2/1 | 5 | 18 | 46 | 75 | 11 | 35 |
| 7 | 10/4/1 | 3 | 20 | 45 | 82 | 13 | 37 |

TABLE 2-continued

Variation of solvent ratio

| Example | DMA/ MeCN/ $H_2O$ | Oxygen [bar] | Time [h] | $X_{1,9\text{-}CHDD}$ [%] | $S_{8\text{-}CHD}$ [%] | $S_{DIKETONE}$ [%] | $Y_{8\text{-}CHD}$ [%] |
|---|---|---|---|---|---|---|---|
| 8 | 7/7/2 | 3 | 18 | 44 | 70 | 8 | 30 |
| 9 | 2/5/1 | 3 | 18 | 35 | 69 | 7 | 24 |

Examples 10 to 16

DMA/MeCN/$H_2O$=10/4/1; Pd(NO$_3$)$_2$.2 $H_2O$; Fe(NO$_3$)$_3$.9 $H_2O$ and Variation of the Reactant Concentration in Pure Oxygen Atmosphere A closable 4 ml glass reactor with screw cap and septum was charged with a solvent system consisting of N,N-dimethylacetamide, acetonitrile and water (DMA/MeCN/$H_2O$=10/4/1; $V_{tot.}$=3 ml), and with 1,9-CHDD (isomer mixture; 0.1-1.0 mmol). Added to this solution were the corresponding amounts of palladium(II) nitrate dihydrate (5.0 mol %); para-toluenesulfonic acid monohydrate (100 mol %) and iron(III) nitrate nonahydrate (10 mol %). The reactor was closed, the septum was pierced with a disposable needle, and the system was brought into an autoclave. The autoclave was purged with oxygen and then the corresponding oxygen pressure was injected (3-5 bar). Thereafter the reaction mixture was stirred intensely in the autoclave at room temperature for 5-20 h. The autoclave was subsequently let down and the reaction solution was made up to a constant volume with tetrahydrofuran and homogenized. The reaction products were analyzed qualitatively and quantitatively using an internal standard (n-hexadecane) on a GC/MS with FID. The results are compiled in Table 3.

TABLE 3

Variation of reactant concentration

| Example | Reactant concentration [mmol] | Oxygen [bar] | Time [h] | $X_{1,9\text{-}CHDD}$ [%] | $S_{8\text{-}CHD}$ [%] | $S_{DIKETONE}$ [%] | $Y_{8\text{-}CHD}$ [%] |
|---|---|---|---|---|---|---|---|
| 10 | 0.1 | 5 | 5 | 26 | 69 | 5 | 18 |
| 11 | 0.2 | 5 | 5 | 39 | 76 | 9 | 29 |
| 12 | 0.2 | 3 | 20 | 45 | 82 | 13 | 37 |
| 13 | 0.4 | 5 | 5 | 34 | 80 | 9 | 27 |
| 14 | 0.5 | 3 | 5 | 35 | 82 | 14 | 28 |
| 15 | 0.5 | 3 | 8 | 41 | 83 | 13 | 33 |
| 16 | 1.0 | 3 | 5 | 32 | 76 | 15 | 25 |

Examples 17 to 20

DMA/MeCN/$H_2O$=10/4/1; Pd(NO$_3$)$_2$.2 $H_2O$; Fe(NO$_3$)$_3$.9 $H_2O$ and Variation of the Catalyst Concentrations in Pure Oxygen Atmosphere A closable 4 ml glass reactor with screw cap and septum was charged with a solvent system consisting of N,N-dimethylacetamide, acetonitrile and water (DMA/MeCN/$H_2O$=10/4/1; $V_{tot.}$=3 ml), and with 1,9-CHDD (isomer mixture; 110 mg; 0.5 mmol). Added to this solution were the corresponding amounts of palladium(II) nitrate dihydrate (5-10 mol %); para-toluenesulfonic acid monohydrate (95 mg; 0.5 mmol) and iron(III) nitrate nonahydrate (10-20 mol %). The reactor was closed, the septum was pierced with a disposable needle, and the system was brought into an autoclave. The autoclave was purged with oxygen and then the corresponding oxygen pressure was injected (3 bar). Thereafter the reaction mixture was stirred intensely in the autoclave at room temperature for 7 h. The autoclave was subsequently let down and the reaction solution was made up to a constant volume with tetrahydrofuran and homogenized. The reaction products were analyzed qualitatively and quantitatively using an internal standard (n-hexadecane) on a GC/MS with FID. The results are compiled in Table 4.

TABLE 4

Variation of catalyst concentration

| Example | Pd(II) concentration [mol %] | Fe(III) concentration [mol %] | $X_{1,9\text{-}CHDD}$ [%] | $S_{8\text{-}CHD}$ [%] | $S_{DIKETONE}$ [%] | $Y_{8\text{-}CHD}$ [%] |
|---|---|---|---|---|---|---|
| 17 | 5 | 10 | 36 | 79 | 11 | 28 |
| 18 | 5 | 20 | 37 | 65 | 6 | 24 |
| 19 | 10 | 10 | 62 | 71 | 17 | 44 |
| 20 | 10 | 20 | 63 | 63 | 14 | 39 |

The invention claimed is:
1. A process for preparing unsaturated macrocyclic monoketones, comprising the following steps:
   (a) providing macrocyclic dienes having a ring size of at least 9 carbon atoms;
   (b) contacting the starting materials from step (a) with
      (b1) a palladium(II) salt and/or a palladium(II) complex; and
      (b2) an oxidizing agent; and
      (b3) a solvent; and optionally
      (b4) a ligand; and optionally
      (b5) a co-catalyst; and optionally
      (b6) an acid,
   wherein the co-catalyst (b5) comprises a divalent or trivalent iron salt which is different from FeSO$_4$.

2. The process of claim 1, wherein the solvent (b3) is a polar aprotic solvent.

3. The process of claim 1, wherein the palladium(II) salt and/or the palladium(II) complex (b1) is selected from the group consisting of palladium bromide, palladium acetate, palladium trifluoroacetate, palladium benzoate, palladium nitrate, palladium sulfate, tetrakis(acetonitrile)palladium(II) tetrafluoroborate and tetrakis(acetonitrile)palladium(II) bis(trifluoromethanesulfonate).

4. The process of claim 1, wherein the palladium(II) salt and/or the palladium(II) complex (b1) form, with a bidentate ligand (b4), a palladium compound of the formula (I) and/or of the formula (II)

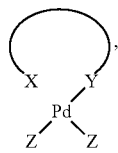
I where X and Y each independently of one another are N,N, O,N or O,O; and where Z independently at each occurrence is a halogen, acetate, trimethylacetate, trifluoromethylacetate, MeCN, PhCN, $NO_2$, NO, nitrate, nitrite or sulfate;

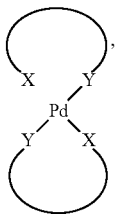
II where X and Y each independently of one another are O,O, N,N or O,N.

5. The process of claim 4, wherein the palladium compound is added at a concentration of 0.01 to 25 mol %, based on the starting material (a).

6. The process of claim 1, wherein the oxidizing agent (b2) is an oxygen-containing gas.

7. The process of claim 6, wherein the oxygen-containing gas comprises oxygen at a concentration of 1 to 100 vol %.

8. The process of claim 1 wherein the process is carried out at temperatures of between 0° C. and 100° C.

9. The process of claim 1, wherein the co-catalyst (b5) and the acid (b6) are necessarily present.

10. The process of claim 9, wherein
   (i) the co-catalyst (b5) comprises at least one further component selected from the group consisting of benzoquinones, naphthoquinones, anthraquinones, molybdatophosphoric acid, molybdatovanadatophosphoric acids, tungstomolybdatophosphoric acids, tungstovanadatophosphoric acids, phthalocyanine complexes, $FeSO_4$, CuCl, $CuCl_2$, $CuSO_4$, $VOSO_4$, and
   (ii) the acid (b) is a Brønsted acid or Lewis acid.

11. The process of claim 10, wherein the co-catalyst (b5) is added at a concentration of 1 to 300 mol %, based on the starting material (a).

12. The process of claim 10, wherein the acid (b6) is added at a concentration of 5 to 500 mol %, based on the starting material (a).

13. The process of claim 9, wherein the palladium(II) salt and/or the palladium(II) complex (b1) is added at a concentration of 0.01 to 20 mol %, based on the starting material (a).

14. The process of claim 10, wherein the process is carried out at temperatures between 0° C. and 100° C.

15. The process of claim 1, wherein the divalent or trivalent iron salt is iron (III) nitrate.

16. The process of claim 2, wherein the polar aprotic solvent is selected from the group consisting of N,N-disubstituted open-chain and cyclic acid amides, aliphatic, cycloaliphatic or aromatic nitriles, or linear and cyclic ethers, cyclic carbonates and lactones.

17. The process of claim 5, wherein the palladium compound is added at a concentration of 1 to 20 mol % based on the starting material (a).

18. The process of claim 13, wherein the palladium(II) salt and/or the palladium(II) complex (b1) is added at a concentration of 0.5 to 10 mol % based on the starting material (a).

19. The process of claim 13, wherein the palladium(II) salt and/or the palladium(II) complex (b1) is added at a concentration of 1 to 5 mol % based on the starting material (a).

20. The process of claim 16, wherein the polar aprotic solvent is selected from the group consisting of dimethylformamide, dimethylacetamide, diethylacetamide, dimethylpropionamide, N-methylpyrrolidone, acetonitrile, propionitrile or benzonitrile.

* * * * *